US008163504B2

(12) United States Patent
Mallat et al.

(10) Patent No.: US 8,163,504 B2
(45) Date of Patent: Apr. 24, 2012

(54) COMBINATION OF SPLA2 ACTIVITY AND OXPL/APOB CARDIOVASCULAR RISK FACTORS FOR THE DIAGNOSIS/PROGNOSIS OF A CARDIOVASCULAR DISEASE/EVENT

(75) Inventors: Ziad Mallat, Herbeville (FR); Alain Tedgui, Paris (FR); Sotirios Tsimikas, San Diego, CA (US); Joseph Witztum, San Diego, CA (US)

(73) Assignees: INSERM (Institut National de la Sante et de la Recherche Medicale), Paris (FR); The Regents of the University of California, Oakland, CA (US); Universite Paris Diderot-Paris 7, Paris (FR)

( * ) Notice: Subject to any disclaimer, the term of this patent is extended or adjusted under 35 U.S.C. 154(b) by 0 days.

(21) Appl. No.: 13/063,303

(22) PCT Filed: Oct. 2, 2009

(86) PCT No.: PCT/EP2009/062852

§ 371 (c)(1),
(2), (4) Date: May 26, 2011

(87) PCT Pub. No.: WO2010/037860

PCT Pub. Date: Apr. 8, 2010

(65) Prior Publication Data

US 2011/0229919 A1 Sep. 22, 2011

Related U.S. Application Data

(60) Provisional application No. 61/102,485, filed on Oct. 3, 2008.

(30) Foreign Application Priority Data

Oct. 27, 2008 (WO) .. INTELL PCT/IB2008/055368

(51) Int. Cl.
*G01N 33/53* (2006.01)

(52) U.S. Cl. .......................... 435/7.1; 435/7.2; 436/518

(58) Field of Classification Search ........................ None
See application file for complete search history.

(56) References Cited

U.S. PATENT DOCUMENTS 7,939,287 B2 5/2011 Tsimikas et al.

FOREIGN PATENT DOCUMENTS

EP 1884571 A 2/2008

OTHER PUBLICATIONS

Mayr et al. J. Am. Coll. Cardiol. (2006) 47:2436-43.*
Rajman et al. (Br. J. Clin. Pharmacology 1999 vol. 48, p. 125-133).*
Kiechl Stefan et al: "Oxidized phospholipids, lipoprotein(a), lipoprotein-associated phospholipase A2 activity, and 10-year cardiovascular outcomes: prospective results from the Bruneck study. "Arteriosclerosis, Thrombosis, and Vascular Biology Aug 2007, vol. 27, No. 8, pp. 1788-1795, XP002518615.
Tsimikas Sotirios et al:"New insights into the role of lipoprotein(a)-associated lipoprotein-associated phospholipase A2 in atherosclerosis and cardiovascular disease", Arteriosclerosis, Thrombosis, and Vascular Biology Oct. 2007, vol. 27, No. 10, pp. 2094-2099, XP002518616.
Ky B et al: "The Influence of Pravastatin and Atorvastatin on Markers of Oxidative Stress in Hypercholesterolemic Humans", Journal of the American College of Cardiology, vol. 51, No. 17, Apr. 29, 2008, pp. 1653-1662, XP022619010.
Mallat et al: "Circulating Secretory Phospholipase A2 Activity Predicts Recurrent Events in Patients With Severe Acute Coronary Syndromes", Journal of The American College of Cardiology, vol. 46, No. 7, Oct. 4, 2005, pp. 1249-1257, XP005095766.
Tselepis Alexandros D et al:"Inflammation, bioactive lipids and atherosclerosis: potential roles of a lipoprotein-associated phospholipase A2, platelet activating factor-acetylhydrolase", Atherosclerosis. Supplements Dec. 2002, vol. 3, No. 4, pp. 57-68, XP002518617.
International Search Report, dated Jan. 27, 2010, in PCT/EP2009/062852.

* cited by examiner

*Primary Examiner* — Jacob Cheu
(74) *Attorney, Agent, or Firm* — Young & Thompson

(57) ABSTRACT

A method of identifying a subject having or at risk of having or developing a cardiovascular disease and/or a cardiovascular event, includes:

measuring, in a sample obtained from the subject, at least two cardiovascular risk factors:
- a) sPLA2 activity and
- b) oxidized phospholipids on apolipoprotein B-100 particles (OxPL/apoB), combining the measurements, the combined value of sPLA2 activity and OxPL/apoB being indicative of having or a risk of having or developing a cardiovascular disease and/or cardiovascular event.

10 Claims, 8 Drawing Sheets

Baseline characteristics

| | Men and women | | |
|---|---|---|---|
| n | 1764 | 769 | |
| Male sex | 61.6 (1086) | 62.8 (483) | Matched |
| Age, years | 65 ± 7 | 65 ± 7 | Matched |
| Body mass index, kg/m2 | 26.2 ± 3.5 | 27.2 ± 3.8 | < 0.001 |
| Waist, cm | 91 ± 11 | 94 ± 12 | < 0.001 |
| Diabetes mellitus | 1.8 (31) | 6.1 (470 | < 0.001 |
| Smoking - current | 8.6 (151) | 15.2 (117) | |
| - previous | 51.1 (901) | 51.9 (399) | < 0.001 |
| - never | 40.4 (712) | 32.9 (253) | |
| Systolic blood pressure, mmHg | 139 ± 18 | 143 ± 19 | < 0.001 |
| Diastolic blood pressure, mmHg | 83 ± 11 | 86 ± 12 | < 0.001 |
| Total cholesterol, mmol/l | 6.3 ± 1.1 | 6.5 ± 1.2 | < 0.001 |
| LDL-cholesterol, mmol/l | 4.1 ± 1.0 | 4.3 ± 1.1 | < 0.001 |
| HDL-cholesterol, mmol/l | 1.4 ± 0.4 | 1.3 ± 0.4 | < 0.001 |
| Triglycerides, mmol/l | 1.6 (1.2-2.2) | 1.9 (1.4-2.6) | < 0.001 |
| Apolipoprotein A-I, mg/dl | 163 ± 29 | 155 ± 29 | < 0.001 |
| Apolipoprotein B, mg/dl | 128 ± 30 | 136 ± 31 | < 0.001 |
| C-reactive protein | 1.5 (0.7-3.1) | 2.2 (1.0-4.9) | < 0.001 |
| Myeloperoxidase | 521 (338-837) | 551 (352-874) | 0,07 |
| sPLA2 | 10.6 ± 8.4 | 12.4 ± 10.6 | < 0.001 |
| sPLA2 activity | 4.5 ± 1.2 | 4.8 ± 1.5 | < 0.001 |
| Lp-PLA2 activity | 51 ± 16 | 53 ± 16 | 0,002 |
| OxPL/apoB | 1667 (1141-2647) | 1899 (1242-3250) | < 0.001 |

Figure 1

OR's unadjusted

| | | Lp-PLA2 tertiles | | |
|---|---|---|---|---|
| | | T1 | T2 | T3 |
| | T1 | 1,00 | 1.26 (0.84-1.90) | 1.53 (1.03-2.28) |
| OxPL/apoB tertiles | T2 | 1.13 (0.75-1.69) | 1.79 (1.20-2.66) | 1.72 (1.16-2.55) |
| | T3 | 1.75 (1.18-2.59) | 2.08 (1.40-3.08) | 2.22 (1.51-3.27) |

| | | sPLA2 activity tertiles | | |
|---|---|---|---|---|
| | | T1 | T2 | T3 |
| | T1 | 1,00 | 1.44 (0.94-2.23) | 2.87 (1.91-4.32) |
| OxPL/apoB tertiles | T2 | 1.35 (0.87-2.08) | 2.26 (1.48-3.45) | 2.67 (1.78-3.99) |
| | T3 | 1.99 (1.31-3.02) | 2.40 (1.60-3.60) | 4.34 (2.84-6.64) |

Figure 2

OR's adjusted for Framingham Risk Score

| | Lp-PLA2 tertiles T1 | T2 | T3 |
|---|---|---|---|
| T1 | 1,00 | 1.08 (0.71-1.63) | 1.22 (0.81-1.86) |
| OxPL/apoB tertiles T2 | 1.09 (0.72-1.66) | 1.64 (1.09-2.47) | 1.50 (1.00-2.25) |
| T3 | 1.66 (1.10-2.50) | 1.93 (1.29-2.90) | 1.86 (1.25-2.79) |

| | sPLA2 activity tertiles T1 | T2 | T3 |
|---|---|---|---|
| T1 | 1,00 | 1.30 (0.84-2.01) | 2.32 (1.53-3.53) |
| OxPL/apoB tertiles T2 | 1.33 (0.86-2.07) | 2.16 (1.41-3.31) | 2.27 (1.51-3.42) |
| T3 | 1.93 (1.27-2.96) | 2.21 (1.46-3.35) | 3.67 (2.38-5.65) |

Figure 3

| | Area under ROC (95% CI) |
|---|---|
| FRS | 0.587 (0.562-0.611) |
| FRS, oxPL | 0.599 (0.576-0.624) |
| FRS, Lp-PLA2 activity | 0.589 (0.565-0.613) |
| FRS, oxPL, Lp-PLA2 activity | 0.602 (0.579-0.626) |
| FRS, sPLA2 activity | 0.619 (0.596-0.643) |
| FRS, oxPL, sPLA2 activity | 0.627 (0.604-0.651) |
| FRS, oxPL, sPLA2 activity, CRP | 0.636 (0.612-0.661) |

Figure 4

| | | OxPL/apoB | | |
|---|---|---|---|---|
| | | T1 | T2 | T3 |
| | T1 | 1.00 | 1.26 (0.81-1.98) | 1.75 (1.14-2.70) |
| **$sPLA_2$ activity** | T2 | 1.16 (0.74-1.80) | 2.10 (1.36-3.25) | 2.04 (1.33-3.13) |
| | T3 | 2.10 (1.36-3.25) | 2.06 (1.36-3.13) | 3.46 (2.22-5.42) |
| | T1 | 1.00 | 1.08 (0.69-1.67) | 1.69 (1.10-2.59) |
| **$sPLA_2$ mass** | T2 | 1.18 (0.77-1.79) | 1.63 (1.07-2.47) | 1.81 (1.20-2.74) |
| | T3 | 1.47 (0.96-2.27) | 1.96 (1.30-2.96) | 2.39 (1.58-3.61) |
| | T1 | 1.00 | 1.09 (0.71-1.68) | 1.60 (1.04-2.45) |
| **Lp-$PLA_2$ activity** | T2 | 0.95 (0.61-1.47) | 1.70 (1.11-2.61) | 1.83 (1.19-2.81) |
| | T3 | 1.13 (0.72-1.77) | 1.28 (0.82-1.97) | 1.66 (1.08-2.56) |

| | Area under ROC (95% CI) |
|---|---|
| FRS | 0.584 (0.559-0.610) |
| FRS, OxPL/apoB | **0.597** (0.572-0.623) |
| FRS, Lp-PLA2 | 0.587 (0.562-0.613) |
| FRS, CRP | 0.605 (0.580-0.630) |
| FRS, sPLA2 mass | 0.609 (0.584-0.634) |
| FRS, sPLA2 activity | **0.618** (0.593-0.642) |
| FRS, OxPL/apoB, Lp-PLA2 | 0.601 (0.575-0.626) |
| **FRS, OxPL/apoB, sPLA2 activity** | **0.626** (0.601-0.651) |
| FRS, OxPL/apoB, sPLA2 mass | 0.619 (0.594-0.644) |
| FRS, OxPL/apoB, CRP | 0.613 (0.588-0.638) |
| FRS, OxPL/apoB, sPLA2 activity, Lp-PLA2 | 0.627 (0.606-0.652) |
| FRS, OxPL/apoB, sPLA2 activity, CRP | 0.636 (0.612-0.660) |
| FRS, OxPL/apoB, sPLA2 activity, sPLA2 mass | 0.637 (0.613-0.662) |

Figure 6

COMBINATION OF SPLA2 ACTIVITY AND OXPL/APOB CARDIOVASCULAR RISK FACTORS FOR THE DIAGNOSIS/PROGNOSIS OF A CARDIOVASCULAR DISEASE/EVENT

FIELD OF THE INVENTION

The invention relates to the use of a combination of sPLA2 activity and OxPL/apoB cardiovascular risk factors for the diagnosis/prognosis of a cardiovascular disease/event or for the monitoring of a cardiovascular disease.

BACKGROUND OF THE INVENTION

A key problem in treating vascular diseases is proper diagnosis. Often the first sign of the disease is sudden death. For example, approximately half of all individuals who die of coronary artery disease die suddenly, Furthermore, for 40-60% of the patients who are eventually diagnosed as having coronary artery disease, myocardial infarction is the first presentation of the disease. Unfortunately, approximately 40% of those initial events go unnoticed by the patient. Because of our limited ability to provide early and accurate diagnosis followed by aggressive treatment, cardiovascular diseases (CD) remain the primary cause of morbidity and mortality worldwide. Patients with CD represent a heterogeneous group of individuals, with a disease that progresses at different rates and in distinctly different patterns. Despite appropriate evidence-based treatments for patients with CD, recurrence and mortality rates remain high. Also, the full benefits of primary prevention are unrealized due to our inability to accurately identify those patients who would benefit from aggressive risk reduction.

Whereas certain disease markers have been shown to predict outcome or response to therapy at a population level, they are not sufficiently sensitive or specific to provide adequate clinical utility in an individual patient. As a result, the first clinical presentation for more than half of the patients with coronary artery disease is either myocardial infarction or death.

Physical examination and current diagnostic tools cannot accurately determine an individual's risk for suffering a complication of CD. Known risk factors such as hypertension, hyperlipidemia, diabetes, family history, and smoking do not establish the diagnosis of atherosclerosis disease. Diagnostic modalities which rely on anatomical data (such as coronary angiography, coronary calcium score, CT or MRI angiography) lack information on the biological activity of the disease process and can be poor predictors of future cardiac events. Functional assessment of endothelial function can be nonspecific and unrelated to the presence of atherosclerotic disease process, although some data has demonstrated the prognostic value of these measurements.

Individual biomarkers, such as the lipid and inflammatory markers, have been shown to predict outcome and response to therapy in patients with CD and some are utilized as important risk factors for developing atherosclerotic disease.

Nonetheless, up to this point, no single biomarker is sufficiently specific to provide adequate clinical utility for the diagnosis of CD in an individual patient. Therefore, there is a need for identifying biomarkers or cardiovascular risk factors or combination thereof that provides a more accurate diagnosis/prognosis of CD.

SUMMARY OF THE INVENTION

One object of the invention is a method of identifying a subject having or at risk of having or developing a cardiovascular disease and/or a cardiovascular event, comprising:

measuring, in a sample obtained from said subject, at least two cardiovascular risk factors:
 a) secretory phospholipases A2 (sPLA2) activity and
 b) oxidized phospholipids on apolipoprotein B-100 particles (OxPL/apoB), combining said measurements, the combined value of sPLA2 activity and OxPL/apoB being indicative of having or a risk of having or developing a cardiovascular disease and/or cardiovascular event.

In one embodiment of the invention, said combined value of sPLA2 activity and OxPL/apoB is compared to a reference value.

In another embodiment of the invention, said method further comprises measuring at least one cardiovascular risk factor selected in the group of Framingham Risk Score (FRS), C-reactive protein (CRP), IgM IC ofapoB100 or IgM MDA-LDL, lipoprotein-associated phospholipase A2(Lp-PLA2) and sPLA2 mass.

In one embodiment of the invention, said method is for identifying a subject having or at risk of having or developing a cardiovascular disease and/or a cardiovascular event, said cardiovascular disease and/or cardiovascular event being Metabolic Syndrome, Syndrome X, atherosclerosis, atherothrombosis, coronary artery disease, stable and unstable angina pectoris, stroke, diseases of the aorta and its branches (such as aortic stenosis, thrombosis or aortic aneurysm), peripheral artery disease, peripheral vascular disease, cerebrovascular disease, and any acute ischemic cardiovascular event.

Another object of the invention is a method as described here above, for monitoring the efficacy of a treatment for a cardiovascular disease.

Another object of the invention is a kit for identifying whether a subject has or is at risk of having or developing a cardiovascular disease and/or a cardiovascular event, comprising:

means for measuring sPLA2 activity and
means for measuring OxPL/apoB.

In one embodiment, said kit further comprises means for measuring at least one cardiovascular risk factor selected in the group of Framingham Risk Score (FRS), CRP, IgM IC of apoB100 or IgM MDA-LDL, Lp-PLA2 and sPLA2 mass.

DETAILED DESCRIPTION OF THE INVENTION

Definitions "Cardiovascular disease" or "arteriovascular disease" as defined herein is a general term used to classify numerous conditions affecting the heart, heart valves, blood, and vasculature of the body and encompasses any disease affecting the heart or blood vessels, including, but not limited to, Metabolic Syndrome, Syndrome X, atherosclerosis, atherothrombosis, coronary artery disease, stable and unstable angina pectoris, stroke, diseases of the aorta and its branches (such as aortic stenosis, thrombosis or aortic aneurysm), peripheral artery disease, peripheral vascular disease, cerebrovascular disease, and including, without limitation, any acute ischemic cardiovascular event. Arteriovascular disease as used herein is meant to most commonly refer to the ischemic or pro-ischemic disease, rather than generally to-non-ischemic disease.

"Cardiovascular event" is used interchangeably herein with the term "cardiac event", "acute arteriovascular event", or "Arteriovascular event" and refers to sudden cardiac death, acute coronary syndromes such as, but not limited to, plaque rupture, myocardial infarction, unstable angina, as well as non-cardiac acute arteriovascular events such as blood clots of the leg, aneurysms, stroke and other arteriovascular ischemic events where arteriovascular blood flow and oxygenation is interrupted.

As used herein, "atherosclerosis" and "atherothrombosis" refer to a complex arteriovascular inflammatory disease that develops in response to multiple stimuli and cardiovascular risk factors, and is associated with systemic inflammation. Cells involved in the atherosclerotic process include vascular (endothelial and smooth muscle) cells, monocytes/macrophages, lymphocytes (T, B, NKT), dendritic cells, mast cells and platelets. They secrete or are stimulated by soluble factors including peptides, glycoproteins, proteases and a set of cytokines They are involved in the perpetuation of the inflammatory response, the progression and the destabilization of atherosclerosis, including plaque erosion, rupture and thrombosis. Arteries harden and narrow due to buildup of a material called "plaque" on their inner walls. As the plaque develops and increases in size, the insides of the arteries get narrower ("stenosis") and less blood can flow through them. Stenosis or plaque rupture may cause partial or complete occlusion of the affected vasculature. Tissues supplied by the vasculature are thus deprived of their source of oxygenation (ischemia) and cell death (apoptosis/necrosis) can occur.

"CAD" or "coronary artery disease" is an arteriovascular disease which occurs when the arteries that supply blood to the heart muscle (the coronary arteries) become atherosclerotic, calcified and/or narrowed. Eventually, blood flow to the heart muscle is reduced, and, because blood carries much-needed oxygen, the heart muscle is not able to receive the amount of oxygen it needs, and often undergoes necrosis. CAD is due to atherosclerosis and atherothrombosis of the blood vessels that supply the heart with oxygen-rich blood and leads to acute coronary syndromes (ACS), myocardial infarction (heart attack), angina (stable and unstable). An estimated 13 million Americans are currently diagnosed with CAD, with approximately 7 million being the survivors of past acute events. Over 1 million new acute CAD events occur each year, many resulting in death. The lifetime risk of CAD after age 40 is 49 percent for men and 32 percent for women. Subjects who are deemed clinically to be at low risk or no risk for developing arteriovascular disease such as CAD often exhibit none or few of the traditional risk factors for the arteriovascular disease, but nevertheless may still be at risk for an acute arteriovascular event. Approximately 20% of all acute CAD events occur in subjects with none of the traditional risk factors, and the majority of all acute CAD occur in subjects who have not been previously diagnosed with CAD. Often these subjects do not exhibit the symptoms of an acute CAD event, i.e. shortness of breath and/or chest pain, until the actual occurrence of such an acute event. A substantial detection gap remains for those who are at risk for an acute CAD event yet are asymptomatic, without traditional risk factors, or are currently deemed clinically to be at low risk and have not yet been diagnosed with CAD. "CVD" or "cerebrovascular disease" is an arteriovascular disease in the blood vessels that feed oxygen-rich blood to the face and brain, such as atherosclerosis and atherothrombosis. This term is often used to describe "hardening" of the carotid arteries, which supply the brain with blood. It is a common comorbid disease with CAD and/or PAD. It is also referred to as an ischemic disease, or a disease that causes a lack of blood flow. CVD encompasses disease states such as "cerebrovascular ischemia," "acute cerebral infarction," "stroke," "ischemic stroke," "hemorrhagic stroke," "aneurysm," "mild cognitive impairment (MCI)" and "transient ischemic attacks" (TIA). Ischemic CVD is believed to closely relate to CAD and PAD; non-ischemic CVD may have multiple pathophysiologies. An estimated 5 million Americans are the survivors of past diagnosed acute CVD events, with an estimated 700 thousand acute CVD events occurring each year. As disclosed herein, subjects deemed to be at low risk or no risk of CVD based on clinical assessments of traditional arteriovascular disease risk factors, or without symptoms such as TIAs, MCI or severe headache, may still be at risk for an acute CVD event.

"PAD" or "peripheral artery disease" encompasses disease states such as atherosclerosis and atherothrombosis that occur outside the heart and brain. It is a common comorbid disease with CAD. Subjects who are deemed to be at low risk or no risk of PAD based upon an assessment of traditional risk factors of PAD (or arteriovascular disease), or who are asymptomatic for PAD or an arteriovascular disease may nevertheless be at risk for an arteriovascular event, even in the absence of claudication. Claudication can be defined as pain or discomfort in the muscles of the legs occurring due to a decreased amount of blood flowing to a muscle from narrowing of the peripheral arteries, producing ischemia and often arterial occlusion, causing skeletal muscle and limb necrosis. The pain or discomfort often occurs when walking and dissipates under resting conditions (intermittent claudication). Pain, tightness, cramping, tiredness or weakness is often experienced as a result of claudication. PAD not only causes the hemodynamic alterations common in CAD, but also results in metabolic changes in skeletal muscle. When PAD has progressed to severe chronic and acute peripheral arterial occlusion, surgery and limb amputation often become the sole therapeutic options. PAD is widely considered to be an underdiagnosed disease, with the majority of confirmed diagnoses occurring only after symptoms are manifested, or only with other arteriovascular disease, and irreversible arteriovascular damage due to such ischemic events has already occurred.

"Cardiovascular Risk Factor" encompasses one or more biomarker whose level is changed in subjects having a cardiovascular disease or predisposed to developing a cardiovascular disease, or at risk of a cardiovascular event.

"Risk" in the context of the present invention, relates to the probability that an event will occur over a specific time period, as in the conversion to arteriovascular events, and can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula p/(1-p) where p is the probability of event and (1-p) is the probability of no event) to no-conversion.

"Risk evaluation," or "evaluation of risk" in the context of the present invention encompasses making a prediction of the probability, odds, or likelihood that an event or disease state may occur, the rate of occurrence of the event or conversion from one disease state to another, i.e., from a normal condition to an arteriovascular condition or to one at risk of developing an arteriovascular event, or from at risk of an arteriovascular event to a more stable arteriovascular condition. Risk evaluation can also comprise prediction of future clinical parameters, traditional laboratory risk factor values, or other indices of arteriovascular disease, such as coronary calcium scores, other imaging or treadmill scores, passive or provocative tesing results, arteriovasculature percentage stenosis or occlusion and other measurements of plaque burden and activity, either in absolute or relative terms in reference to a previously measured population. The methods of the present invention may be used to make continuous or categorical measurements of the risk of conversion to arteriovascular disease and events, thus diagnosing and defining the risk spectrum of a category of subjects defined as being at risk for an arteriovascular event. In the categorical scenario, the invention can be used to discriminate between normal and other subject cohorts at higher risk for arteriovascular events. In other embodiments, the present invention may be used so as to discriminate those at risk for developing an arteriovascular event from those having arteriovascular disease, or those having arteriovascular disease from normal.

A "sample" in the context of the present invention is a biological sample isolated from a subject and can include, by way of example and not limitation, bodily fluids and/or tissue extracts such as homogenates or solubilized tissue obtained from a subject. Tissue extracts are obtained routinely from tissue biopsy and autopsy material. Bodily fluids useful in the present invention include blood, urine, saliva or any other bodily secretion or derivative thereof. As used herein "blood" includes whole blood, plasma, serum, circulating cells, constituents, or any derivative of blood.

"Clinical parameters or indicia" encompasses all non-sample or non-analyte biomarkers of subject health status or other characteristics, such as, without limitation, age (Age), ethnicity (RACE), gender (Sex), diastolic blood pressure (DBP) and systolic blood pressure (SBP), family history (FamHX), height (HT), weight (WT), waist (Waist) and hip (Hip) circumference, body-mass index (BMI), as well as others such as Type I or Type II Diabetes Mellitus or Gestational Diabetes Mellitus (DM or GDM, collectively referred to here as Diabetes), and resting heart rate.

A "subject" in the context of the present invention is preferably a mammal. The mammal can be a human, non-human primate, mouse, rat, dog, cat, horse, or cow, but are not limited to these examples. Mammals other than humans can be advantageously used as subjects that represent animal models of arteriovascular disease or arteriovascular events. A subject can be male or female. A subject can be one who has been previously diagnosed or identified as having arteriovascular disease or an arteriovascular event, and optionally has already undergone, or is undergoing, a therapeutic intervention for the arteriovascular disease or arteriovascular event. Alternatively, a subject can also be one who has not been previously diagnosed as having arteriovascular disease. For example, a subject can be one who exhibits one or more risk factors for arteriovascular disease, or a subject who does not exhibit arteriovascular risk factors, or a subject who is asymptomatic for arteriovascular disease or arteriovascular events. A subject can also be one who is suffering from or at risk of developing arteriovascular disease or an arteriovascular event.

A "formula," "algorithm," or "model" is any mathematical equation, algorithmic, analytical or programmed process, or statistical technique that takes one or more continuous or categorical inputs (herein called "parameters") and calculates an output value, sometimes referred to as an "index" or "index value." Non-limiting examples of "formulas" include sums, ratios, and regression operators, such as coefficients or exponents, biomarker value transformations and normalizations (including, without limitation, those normalization schemes based on clinical parameters, such as gender, age, or ethnicity), rules and guidelines, statistical classification models, and neural networks trained on historical populations. Of particular use in combining Cardiovascular Risk Factor and other biomarkers are linear and non-linear equations and statistical classification analyses to determine the relationship between levels of Cardiovascular Risk Factor detected in a subject sample and the subject's risk of cardiovascular disease. In panel and combination construction, of particular interest are structural and synactic statistical classification algorithms, and methods of risk index construction, utilizing pattern recognition features, including established techniques such as cross-correlation, Principal Components Analysis (PCA), factor rotation, Logistic Regression (LogReg), Linear Discriminant Analysis (LDA), Eigengene Linear Discriminant Analysis (ELDA), Support Vector Machines (SVM), Random Forest (RF), Recursive Partitioning Tree (RPART), as well as other related decision tree classification techniques, Shrunken Centroids (SC), StepAIC, Kth-Nearest Neighbor, Boosting, Decision Trees, Neural Networks, Bayesian Networks, Support Vector Machines, and Hidden Markov Models, among others. Other techniques may be used in survival and time to event hazard analysis, including Cox, Weibull, Kaplan-Meier and Greenwood models well known to those of skill in the art.

"Measuring" or "measurement," or alternatively "detecting" or "detection," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's non-analyte clinical parameters.

THE INVENTION

One object of the invention is a method of identifying a subject having or at risk of having or developing a cardiovascular disease and/or a cardiovascular event, comprising:

measuring, in a sample obtained from said subject, at least two cardiovascular risk factors:
- a) sPLA2 activity and
- b) oxidized phospholipids on apolipoprotein B-100 particles (OxPL/apoB), combining said measurements, the combined value of sPLA2 activity and OxPL/apoB being indicative of having or a risk of having or developing a cardiovascular disease and/or cardiovascular event.

According to the invention, combining said measurements using a statistical analysis results in obtaining a combined value, which is indicative of having or a risk of having or developing a cardiovascular disease and/or cardiovascular event.

In one embodiment of the invention, the subject may be a substantially healthy subject, which means that the subject has not been previously diagnosed or identified as having or suffering from a cardiovascular disease, or that has not developed a cardiovascular event. In another embodiment, the subject may also be one that is asymptomatic for the cardiovascular disease. As used herein, an "asymptomatic" subject refers to a subject that do not exhibit the traditional symptoms of a cardiovascular disease or event, including, but not limited to, chest pain and shortness of breath for CAD, claudication for PAD, and TIAS, MCI and severe headache for CVD.

In another embodiment of the invention, the subject may be one that is at risk of having or developing a cardiovascular disease or cardiovascular event, as defined by clinical and biological indicia such as for example: age, gender, LDL concentration, HDL concentration, triglyceride concentration, blood pressure, body mass index, CRP concentration, coronary calcium score, waist circumference, tobacco smoking status, previous history of cardiovascular disease, family history of cardiovascular disease, heart rate, fasting insulin concentration, fasting glucose concentration, diabetes status, and use of high blood pressure medication.

In another embodiment of the invention, the subject may be one that has been previously diagnosed or identified for a cardiovascular disease or cardiovascular event, such as for example chronic ischemic disorders without myocardial necrosis (for example stable or effort angina pectoris), acute ischemic disorders without myocardial necrosis (for example unstable angina pectoris), ischemic disorders with myocardial necrosis (for example ST segment evaluation myocardial infarction or non-ST segment elevation myocardial infarction).

Tissue ischemia is often defined in relative terms and occurs when the needs in oxygen exceed the delivery of oxygen to tissues. There is an imbalance between tissue (myocardial for example) oxygen demands and supply. This condition of oxygen deprivation may be accompanied by inadequate removal of metabolites consequent to reduced perfusion. Myocardial ischemia can be diagnosed clinically (chest pain for example), biologically (increase in myeloperoxidase activity for example), metabolically, using scintigraphy, by analyzing regional wall motion disorders or by use of an electrocardiogram (typical modifications of the ST segment, upper or lower ST segment deviation, typical changes in T wave such as T wave inversion or steep symmetric or high amplitude positive T waves). Silent ischemia is typically diagnosed using scintigraphy or a 24h electrocardiogram recording.

Stable and effort angina is typically manifested by a chest pain during exercise and slowly recovers at rest. It usually reflects tissue ischemia during exercise.

Unstable angina is a recent increase in the frequency and/or severity of stable angina, a first episode of angina, or an angina at rest.

Myocardial necrosis is typically diagnosed by an increase in myocardial enzymes (for example troponin I, troponin T, CPK) in the circulating blood.

In another embodiment of the invention, the subject may be one that who shows an improvement in cardiovascular risk factors as a result of treatments and/or therapies for cardiovascular diseases. Such improvements include a reduction in body mass index, a reduction in total cholesterol, a reduction in LDL levels, an increase in HDLC levels, a reduction in systolic and/or diastolic blood pressure, or other aforementioned risk factor or combinations thereof.

In one embodiment of the invention, no onset of ischemic symptom has been diagnosed in the subject. Myocardial ischemia can be diagnosed clinically (chest pain for example), biologically (increase in myeloperoxidase activity for example), metabolically using scintigraphy, by analysing regional wall motion disorders or by use of an electrocardiogram (typical modifications of the ST segment, upper or lower ST segment deviation, typical changes in T wave such as T wave insertion or steep symmetric or high amplitude positive T waves).

In another embodiment, an onset of ischemic symptoms has been diagnosed in the subject.

In one embodiment of the invention, the sample used to measure sPLA2 activity and OxPL/apoB and optionally other cardiovascular risk factors is a blood sample, whole blood, plasma, serum.

According to the invention, sPLA2 activity is measured in said sample. According to the invention, the measure of sPLA2 activity can be performed by a fluorimetric assay according to Radvanyi et al. (1989 Anal Biochem 177: 103-9) as modified by Pernas et al. (1991 Biochem Biophys Res Commun 178: 1298-1305), all incorporated by reference.

In particular, the following assay is used. The 1-hexadecanoyl-2-(1-pyrenedecanoyl)-sn-glycero-3-phosphomethanol sodium salt (Interchim, Montlucon, France) is used as a substrate for sPLA2. The hydrolysis of this substrate by sPLA2 yields 1-pyrenedecanoic acid, which emits fluorescence at 397 nm. A volume (E) of 0.03 ml of the aliquoted plasmas is mixed with 5 nmol of substrate in presence of a 10 mM Tris-HCL pH 8.7, 0.1% albumin, 10 mM CaCl2 in a total volume of 2.5 ml, and fluorescence (F) is measured at 397 nm after one minute. 100% hydrolysis of the substrate is obtained with 0.1 U of bee venom PLA2 (Sigma Chemical Co., France) during one minute, the value of the fluorescence at the end of the one minute reaction (Fmax) thus corresponds to an activity of 2 nmoles/min/ml (Vmax). The activity (A) of the sample (expressed in nmol/ml/min) is given by the following formula: A=(Vmax*F)/(E*Fmax).

The samples are diluted when substrate hydrolysis is above 50%. The hydrolysis of substrate in the absence of plasma is used as negative control and deduced from PLA2 activity. All samples are tested in duplicate. The minimum detectable activity and detection limit is 0.10 nmole/min/ml and the intra and interassay coefficient of variation is lower than 10%.

According to the invention, the measure of sPLA2 activity can be performed by an improved fluorimetric assay, using an automated fluorimetric measurement, with a small sample volume, a modified substrate/enzyme ratio (10 nmoles/U instead of 50 nmoles/U) and a thermostat ruled at 30° C., providing a higher precision and sensitivity (2,7% <within batch coefficient of variation (CV)<3.2% and between batch CV=5.7%) than the previous method (within batch CV<10% and between batch CV<10%) and a substantially shorter time to complete the assay. In particular, the following assay is used for automated measurement. The 1 -hexadecanoyl-2-(1 -pyrenedecanoyl)-sn-glycero-3-phosphomethanol sodium salt (Interchim, Montlucon, France) is used as a substrate for sPLA2. The hydrolysis of this substrate by sPLA2 yields 1-pyrenedecanoic acid, which emits fluorescence at 405 nm. Briefly, 1 nmol of fluorescent substrate in 0.2 ml of buffer substrate (10 mM Tris-HCL pH 8.7, 0.1% albumin, 10 mM CaCl2) was automatically distributed in Black Maxisorp microtitration plate (96 wells). Because the self-quenching properties of the substrate, a low fluorescence is firstly recorded (Fmin) in a Fluostar Optima fluorimeter equipped with a stirring device and thermostat ruled at 30° C. The addition of 30 μl (100 U/mL) of bee venom PLA2 (Sigma Chemical Co., France) leads to a rapid hydrolysis of all substrate (100% of hydrolysis) and an increase in fluorescence to a maximal value (Fmax), corresponding to an activity of 5 nmol/ml. To determine the sPLA2 activity in unknown blood samples, 30 μl of sera (E) were automatically distributed and added to the substrate mixture and the fluorescence was recorded at one minute (F). A two-point procedure was used to measure the corrected fluorescence intensity of each sample and to evaluate the enzymatic activity (expressed in nmol/min/ml). All samples were tested in duplicate. The activity (A) of the sample (expressed in nmol/ml/min) is given by the following formula: A=(Vmax*F)/(E*Fmax).

The hydrolysis of the substrate in the absence of serum is used as negative control and deduced from PLA2 activity. All samples are tested in duplicate. Unless otherwise mentioned, all the numerical values given herein for serum sPLA2 activity are measured according to the above defined assay for automated measurement.

The phospholipase that can be used to perform the assay is a secretory phospholipase or a phospholipase with a known activity and preferably a bee venom phospholipase.

In another embodiment, sPLA2 activity may be determined by a process based on a fluorimetric assay comprising contacting a biological sample containing said sPLA2 and taken from said patient, with a substrate at a concentration from 1 nM to 15 nM, the serum sample volume being from 5 μl to 50 μl and the substrate volume being from 100 μlto 300 μl, at a temperature range from about 15° C. to about 40° C. and preferably 30° C. The phospholipase used could be a phospholipase from bee venom or snake venom like Naja venom, preferably bee venom. It could be a recombinant phospholipase from any species. This assay is described in example 2 of W02008/015546, which is incorporated by reference. The advantage of this method is the small sample volume of substrate used and the thermostating, providing a higher precision and sensitivity.

Alternatively, a variant of the automated fluorimetric measurement as defined above can be used, which enables to alleviate imprecision which might result from a non-specific increase in fluorescence intensity due to other factors in the sample, thus interfering with the measure of sPLA2 activity. This method only differs from the above-defined automated fluorimetric measurement method in that the following formula is used for determining sPLA2 activity:

$$A=F*s/[(\text{Fmax}-\text{Fmin})*V]$$

wherein:

A represents sPLA2 activity expressed in nmol/min/ml;

s represents the quantity of substrate expressed in nmol (usually 1 nmol in a volume of 200 μl of working solution);

V represents the sample volume expressed in ml (usually from 0.30 to 0.50 ml);

(Fmax-Fmin) represents the difference between the maximal fluorescence signal at the end of the reaction in the presence of PLA2 from bee venom and the negative control;

F represents the initial slope, within linear range, of the curve representing fluorescence emission as a function of time, expressed in $min^{-1}$.

This variant of the automated fluorimetric measurement is described in example 4 of WO2008/015546, which is incorporated by reference.

According to the invention, OxPL/apoB is measured in said sample.

Methods for measuring the ratio OxPL/apoB is described in US2006/177435, which is incorporated by reference. Said methods are based on the determination of OxPL level in the sample, the determination of apoB level in the sample, and then calculating the ratio OxPL/apoB.

In one embodiment, the level of OxPL and the level of apoB in the sample obtained from the subject are measured with two or more different biomolecules. The first biomolecule specifically interacts with OxPL and the second biomolecule specifically interacts with apoB. In some aspects, the biomolecules are antibodies, such as, for example, monoclonal antibodies. The antibody that interacts with OxPL may be, for example, E06 or DLH3.

In other aspects, the biomolecules are antigens. In some embodiments, the biomolecules are immobilized to form an array comprising a first set of a plurality of the first biomolecule and a second set of a plurality of the second biomolecule.

Exemplary oxidized phospholipid include oxidized forms of 1-palmitoyl-2-arachidonoyl-sn-glycero-3-phos-phorylcholine (Ox-PAPC), 1-palmitoyl-2-oxovaleroyl-sn-glycero-3-phosphoryl-choline (POVPC), 1-palmitoyl-2-glutaroyl-sn-glycero-3-phosphorylcholine (PGPC), 1-palmitoyl-2-epoxyisoprostane-sn-glycero-3-phosphorylcholine (PEIPC), oxidized 1-stearoyl-2-arachidonoyl-sn-glycero-3-phosphorylcholin-e (Ox-SAPC), 1-stearoyl-2-oxovaleroyl-sn-glycero-3-phosphorylcholine (SOVPC, 1-stearoyl-2-glutaroyl-sn-glycero-3-phosphorylcholine (SGPC), 1-stearoyl-2-epoxyisopro stane-sn-glycero-3-phosphorylcholine (SEIPC), 1-stearoyl-2-arachidonyl-sn-glycero-3-phosphorylethanolamine(Ox-SAPE), 1-stearoyl-2-oxovaleroyl-sn-glycero-3-phosphorylethanolamine(SOVPE), 1-stearoyl-2-glutaroyl-sn-glycero-3-phosphorylethanolamine(SGPE), and 1-stearoyl-2-epoxyisoprostane-sn-glycero-3-phosphorylethanolamine(SEIPE).

As used herein, the terms "biological molecules" and "biomolecules" may be used interchangeably. These terms are meant to be interpreted broadly, and generally encompass polypeptides, peptides, oligosaccharides, polysaccharides, oligopeptides, proteins, oligonucleotides, and polynucleotides. Oligonucleotides and polynucleotides include, for example, DNA and RNA, e.g., in the form of aptamers. Biomolecules also include organic compounds, organometallic compounds, salts of organic and organometallic compounds, saccharides, amino acids, and nucleotides, lipids, carbohydrates, drugs, steroids, lectins, vitamins, minerals, metabolites, cofactors, and coenzymes. Biomolecules further include derivatives of the molecules described. For example, derivatives of biomolecules include lipid and glycosylation derivatives of oligopeptides, polypeptides, peptides, and proteins, such as antibodies. Further examples of derivatives of biomolecules include lipid derivatives of oligosaccharides and polysaccharides, e.g., lipopolysaccharides. An exemplary biochemical test for identifying specific proteins, such as OxPL and apoB, employs a standardized test format, such as the Enzyme Linked Immunosorbent Assay or ELISA test, although the information provided herein may apply to the development of other biochemical or diagnostic tests and is not limited to the development of an ELISA test (see, e.g., Molecular Immunology: A Textbook, edited by Atassi et al. Marcel Dekker Inc., New York and Basel 1984, for a description of ELISA tests). It is understood that commercial assay enzyme-linked immunosorbant assay (ELISA) kits for various plasma constituents are available.

Improved methods for measuring the ratio OxPL/apoB is described in WO01/88547, which is incorporated by reference. Said improved methods are intended to standardize the assay by using a phosphorylcholine (PC). According to said method, an immunoassay can be performed either by first capturing the LDL on a microtiter well by use of an antibody that binds both oxidized and nonoxidized LDL (e. g. anti-apoB), and then detection of the OxLDL by a labelled E06 antibody. Alternatively, E06 antibody can be bound to the bottom of the microtiter well and the amount of OxLDL bound determined by the use of labeled anti-LDL antibody. OxLDL could also be used to coat the microtiter wells and various concentrations of patient sera, putatively containing OxLDL, could be mixed with a constant, limiting amount of labeled (e. g. biotinylated) E06 or T15 to compete for binding to the OxLDL on the plate. For each assay, under standard conditions, a standard curve could be developed using PC as a competing agent. Alternatively, a parallel set of reactions can be run using PC as a source of competing agent rather than patient sera. The PC can be used alone, or linked to a carrier protein, such as bovine serum albumin (BSA) or keyhole limpet hemocyanin (KLH).

According to the invention, the measurements obtained for sPLA2 activity and OxPL/apoB and optionally other cardiovascular risk factors are combined in statistical analysis, wherein the combined value of sPLA2 activity and OxPL/apoB and optionally other cardiovascular risk factors is indicative of having or a risk of having or developing a cardiovascular disease and/or cardiovascular event.

As the skilled artisan will appreciate, there are many ways to use the measurements of two or more risk factors in order to improve the diagnostic/prognostic question under investigation.

In a quite simple, but nonetheless often effective approach, a positive result is assumed if a sample is positive for at least one of the markers investigated. This may be for example the case when diagnosing an infectious disease, like AIDS. Frequently, however, a combination of risk factors is evaluated. Preferably the measurements obtained for sPLA2 activity and OxPL/apoB and optionally other cardiovascular risk factors are mathematically combined and the combined value is correlated to the underlying diagnostic/prognostic question. Risk factor measurements may be combined by any appropriate state of the art mathematical method. Well-known mathematical methods for correlating a marker combination to a disease employ methods like, Discriminant analysis (DA) (i.e. linear-, quadratic-, regularized-DA), Kernel Methods (i.e. SVM), Nonparametric Methods (i.e. k-Nearest-Neighbor Classifiers), PLS (Partial Least Squares), Tree-Based Methods (i.e. Logic Regression, CART, Random Forest Methods, Boosting/Bagging Methods), Generalized Linear Models (i.e. Logistic Regression), Principal Components based Methods (i.e. SIMCA), Generalized Additive Models, Fuzzy Logic based Methods, Neural Networks and Genetic Algorithms based Methods. The skilled artisan will have no problem in selecting an appropriate method to evaluate a marker combination of the present invention.

Preferably the method used in correlating the risk factors combination of the invention to the risk of having or being at risk of having a cardiovascular disease or cardiovascular event is selected from DA (i.e. Linear-, Quadratic-, Regularized Discriminant Analysis), Kernel Methods (i.e. SVM), Nonparametric Methods (i.e. k-Nearest-Neighbor Classifiers), PLS (Partial Least Squares), Tree-Based Methods (i.e. Logic Regression, CART, Random Forest Methods, Boosting Methods), or Generalized Linear Models (i.e. Logistic Regression). Details relating to these statistical methods are found in the following references: Ruczinski, I., Kooperberg C., LeBlanc, M., Logic regression, J. of Computational and Graphical Statistics, 12 (2003) 475-511; Friedman, J. H. , Regularized Discriminant Analysis, J. of the American Statistical Association, 84 (1989) 165-175; Trevor Hastie, Robert Tibshirani and Jerome Friedmann, The Elements of Statistical Learning, Springer Verlag, 2001; Breiman, L., Friedman, J. H., Olshen, R. A., Stone, C. J. (1984) Classification and regression trees, California: Wadsworth; Breiman, L., Random Forests, Machine Learning, 45 (2001) 5-32; Pepe, M. S., The Statistical Evaluation of Medical Tests for Classification and Prediction, Oxford Statistical Science Series, 28 (2003); and Duda, R. O., Hart, P. E., Stork, D. G., Pattern Classification, Wiley Interscience, 2nd Edition (2001).

In one embodiment of the invention, an optimized multivariate cut-off for the underlying combination of risk factors is used to discriminate state A from state B, e.g. diseased from substantially healthy. In this type of analysis, the risk factors are no longer independent but form a risk factor panel. Combining the measurements of sPLA2 activity and OxPL/apoB does significantly improve the diagnostic/prognostic accuracy for cardiovascular disease and/or cardiovascular event as compared to substantially healthy subjects or as compared to subjects which have been diagnosed for a cardiovascular disease or event.

In one embodiment of the invention, the statistical analysis of the measurements of sPLA2 activity and OxPL/apoB and optionally other cardiovascular risk factors is based on the determination of odds ratios (OR) using standard procedures. An odds ratio is calculated by dividing the odds in the test group by the odds in the control group. The odds of an event are calculated as the number of events divided by the number of non-events. If the odds of an event are greater than one the event is more likely to happen than not (the odds of an event that is certain to happen are infinite); if the odds are less than one the chances are that the event won't happen (the odds of an impossible event are zero). In general, the strength of association is reported as odds ratios (OR) (with 95% lower (LCL) and upper (UCL) confidence limit), indicating the factor by which the risk of having a disease or being at risk of having or developing a disease is increased (OR>1). The 95% confidence interval (95% Cl) is the range of numerical values in which we can be confident (to a computed probability, here 95%) that the population value being estimated will be found. Confidence intervals indicate the strength of evidence; where confidence intervals are wide, they indicate less precise estimates of effect. The larger the trial's sample size, the larger the number of outcome events and the greater becomes the confidence that the true relative risk reduction is close to the value stated. Thus the confidence intervals get narrower and "precision" is increased. To confidently accept a calculated OR as reliable, important or clinically significant, the lower boundary of the confidence interval, or lower confidence limit, should be >1 if the OR>1, or the upper boundary of the confidence interval should be <1 if the OR<1.

In another embodiment of the invention, accuracy of a diagnostic/prognostic method is best described by its receiver-operating characteristics (ROC) (see especially Zweig, M. H., and Campbell, G., Clin. Chem. 39 (1993) 561-577). The ROC graph is a plot of all of the sensitivity/specificity pairs resulting from continuously varying the decision thresh-hold over the entire range of data observed.

The clinical performance of a laboratory test depends on its diagnostic accuracy, or the ability to correctly classify subjects into clinically relevant subgroups. Diagnostic accuracy measures the test's ability to correctly distinguish two different conditions of the subjects investigated. Such conditions are for example health and disease.

In each case, the ROC plot depicts the overlap between the two distributions by plotting the sensitivity versus 1—specificity for the complete range of decision thresholds. On the y-axis is sensitivity, or the true-positive fraction [defined as (number of true-positive test results)/(number of true-positive + number of false-negative test results)]. This has also been referred to as positivity in the presence of a disease or condition. It is calculated solely from the affected subgroup. On the x-axis is the false-positive fraction, or 1—specificity [defined as (number of false-positive results)/(number of true-negative + number of false-positive results)]. It is an index of specificity and is calculated entirely from the unaffected subgroup. Because the true- and false-positive fractions are calculated entirely separately, by using the test results from two different subgroups, the ROC plot is independent of the prevalence of disease in the sample. Each point on the ROC plot represents a sensitivity/1-specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. (If the ROC plot falls completely below the 45° diagonal, this is easily remedied by reversing the criterion for "positivity" from "greater than" to "less than" or vice versa). Qualitatively, the closer the plot is to the upper left corner, the higher the overall accuracy of the test.

One convenient goal to quantify the diagnostic accuracy of a laboratory test is to express its performance by a single number. The most common global measure is the area under the ROC plot. By convention, this area is always 0.5 (if it is not, one can reverse the decision rule to make it so). Values range between 1.0 (perfect separation of the test values of the two groups) and 0.5 (no apparent distributional difference between the two groups of test values). The area does not depend only on a particular portion of the plot such as the point closest to the diagonal or the sensitivity at 90% specificity, but on the entire plot. This is a quantitative, descriptive expression of how close the ROC plot is to the perfect one (area=1.0).

In one embodiment of the invention, the combined value of sPLA2 activity and OxPL/apoB and optionally other risk factors is compared to a reference value.

In one embodiment, the reference value may be an index value or may be derived from one ore more risk prediction algorithms or computed indices for the cardiovascular disease and/or cardiovascular event. A reference value can be relative to a number or value derived from population studies, including without limitation, such subjects having similar body mass index, total cholesterol levels, LDL/HDL levels, systolic or diastolic blood pressure, subjects of the same or similar age range, subjects in the same or similar ethnic group, subjects having family histories of atherosclerosis, atherothrombosis, or CAD, PAD, or CVD, or relative to the starting sample of a subject undergoing treatment for an arteriovascular disease, such as atherosclerosis, atherothrombosis, CAD, PAD, or CVD.

Such reference values can be derived from statistical analyses and/or risk prediction data of populations obtained from mathematical algorithms and computed indices of arteriovascular disease, such as but not limited to, algorithms reported in the Framingham Study, NCEP/ATP III, among others. Cardiovascular Risk Factor reference value can also be constructed and used using algorithms and other methods of statistical and structural classification.

In one embodiment of the present invention, the reference value is derived from the combination of OxPL/apoB and sPLA2 activity and optionally others cardiovascular risk factors in a control sample derived from one or more subjects who are substantially healthy as defined here above. Such subjects who are substantially healthy lack traditional risk factors for a cardiovascular disease: for example, those subjects have a serum cholesterol level less than 200 mg/dl, systolic blood pressure less than or equal to 120 mm Hg, diastolic blood pressure less than or equal to 80 mm Hg, non-current smoker, no history of diagnosed diabetes, no previously diagnosed acute coronary syndrome or hypertension, among other aforementioned other risk factors, or can be verified by another invasive or non-invasive diagnostic test of cardiovascular disease known in the art, such as but not limited to, electrocardiogram (ECG), carotid B-mode ultrasound (for intima-medial thickness measurement), electron beam computed tomography (EBCT), coronary calcium scoring, multi-slice high resolution computed tomography, nuclear magnetic resonance, stress exercise testing, angiography, intra- vascular ultrasound (IVUS), other contrast and/or radioisotopic imaging techniques, or other provocative testing techniques.

In another embodiment, such subjects are monitored and/or periodically retested for a diagnostically relevant period of time ("longitudinal studies") following such test to verify continued absence from cardiovascular disease or acute cardiovascular events (disease or event free survival). Such period of time may be one year, two years, two to five years, five years, five to ten years, ten years, or ten or more years from the initial testing date for determination of the reference value. Furthermore, retrospective measurement of OxPL/apoB and sPLA2 activity levels in properly banked historical subject samples may be used in establishing these reference values, thus shortening the study time required, presuming the subjects have been appropriately followed during the intervening period through the intended horizon of the product claim.

In another embodiment, a reference value can also be derived from the combination of OxPL/apoB and sPLA2 activity and optionally other cardiovascular risk factors in a sample derived from one or more subject who (1) has been previously diagnosed or identified for a cardiovascular disease or cardiovascular event by one of the above invasive or non-invasive techniques, or who has suffered from an cardiovascular event or plaque rupture, and (2) has not experienced a recurrent cardiovascular event.

In another embodiment, a reference value can also be derived from the combination of OxPL/apoB and sPLA2 activity and optionally other cardiovascular risk factors in a sample derived from one or more subject who is at high risk for developing a cardiovascular event, or who is at high risk for developing an atherosclerotic or atherothrombotic plaque rupture.

In another embodiment of the invention, a reference value can also be derived from the combination of OxPL/apoB and sPLA2 activity and optionally other cardiovascular risk factors in a sample derived from one or more subject who shows an improvement in cardiovascular risk factors as a result of treatments and/or therapies for cardiovascular diseases. Such improvements include a reduction in body mass index, a reduction in total cholesterol, a reduction in LDL levels, an increase in HDLC levels, a reduction in systolic and/or diastolic blood pressure, or other aforementioned risk factor or combinations thereof.

In one embodiment of the invention, the reference value is an index value or a baseline value. An index value or baseline value is derived from one or more subjects who do not have a cardiovascular disease, such as atherosclerosis, atherothrombosis, CAD, PAD, or CVD, or subjects who are asymptomatic for a cardiovascular disease. A baseline value can also be derived from a subject who has shown an improvement in cardiovascular risk factors (as a result of cardiovascular treatments or therapies. Such improvements include, without limitation, a reduction in body mass index, a reduction in total cholesterol, a reduction in LDL levels, an increase in HDLC levels, a reduction in systolic and/or diastolic blood pressure, or combinations thereof In one embodiment of the invention, the method of the invention comprises combining sPLA2 activity and OxPL/apoB with clinical and biological indicia such as age, a history of hypertension, diabetes, myocardial infarction, heart failure, coronary angiography or angioplasty, Killip class, ST-segment deviation, coronary revascularization (angioplasty or coronary artery bypass surgery), and creatinine In another embodiment of the invention, the method of the invention comprises:

measuring, in a sample obtained from said subject, at least two cardiovascular risk factors:

a) sPLA2 activity and b) oxidized phospholipids on apolipoprotein B-100 particles (OxPL/apoB), and at least one cardiovascular risk factor selected in the group of Framingham Risk Score (FRS), CRP, IgM IC (IgM Immune Complexes) of apoB100 or IgM MDA-LDL (IgM Malondialdehyde LDL), Lp-PLA2 activity and sPLA2 mass, combining said measurements, the combined value being indicative of having or a risk of having or developing a cardiovascular disease and/or cardiovascular event.

According to said embodiment, FRS is calculated using a previously reported algorithm, which takes into account age, sex, total cholesterol, HDL-C, systolic and diastolic blood pressure, smoking and the presence of diabetes (Wilson P. W. et al., Circulation. 1998;97:1837-1847, which is incorporated by reference).

According to said embodiment, CRP can be measured by methods known in the art, such as a the method described in Arima et al (Arterioscler Thromb Vasc Biol. 2008 Jul; 28(7): 1385-91) and Ridker et al. (New England Journal of Medecine, 2000, 342:836-843), which are incorporated by reference.

According to said embodiment, IgM IC of apoB100 and IgM MDA-LDL can be measured by methods known in the art such as according to Tsimikas et al (2004, Circulation, 110:1406-1412 and 2003 J. Am. Coll. Cardiol. 41:360-370), which are incorporated by reference.

According to said embodiment, Lp-PLA-2 activity can be measured by methods known in the art such as according to Kiechl et al. (2007, Atherioscler. Thromb. Vasc. Biol. 27:1788-1795), which is incorporated by reference. For example, Lp-PLA2 activity may be measured using a commercially available kit (Azwell Inc) based on the method of Kosaka et al (2000 Clin. Chim. Acta 296:151-161, which is incorporated by reference). LpPLA2 activity may also be measured by the method described in WO2005074604, which is incorporated by reference.

According to said embodiment, sPLA2 mass can be measured using an immunometric assay with a monoclonal antibody specific for sPLA2-IIA (Cayman Chemical Company).

In one embodiment, the method of the invention comprises the combination of sPLA2 activity, OxPL/apoB and FRS measurements.

In another embodiment, the method of the invention comprises sPLA2 activity, OxPL/apoB, FRS and CRP measurements.

In another embodiment, the method of the invention comprises sPLA2 activity, OxPL/apoB, FRS and sPLA2 mass measurements.

According to the invention, the method as described here above is for identifying whether a subject has or is at risk of having or developing a cardiovascular disease and/or a cardiovascular event.

In one embodiment of the invention, said cardiovascular disease and/or cardiovascular event is Metabolic Syndrome, Syndrome X, atherosclerosis, atherothrombosis, coronary artery disease, stable and unstable angina pectoris, stroke, diseases of the aorta and its branches (such as aortic thrombosis or aortic aneurysm), peripheral artery disease, peripheral vascular disease, cerebrovascular disease, and any acute ischemic cardiovascular event.

Optionally, subjects identified as having, or being at increased risk of developing a cardiovascular disease or cardiovascular event are chosen to receive a therapeutic regimen to slow the progression of a cardiovascular disease, or decrease or prevent the risk of developing a cardiovascular disease or a cardiovascular event.

According to the invention, the method as described here above is for monitoring a cardiovascular disease or event in a subject in need thereof, said cardiovascular disease or event being Metabolic Syndrome, Syndrome X, atherosclerosis, atherothrombosis, coronary artery disease, stable and unstable angina pectoris, stroke, diseases of the aorta and its branches (such as aortic thrombosis or aortic aneurysm), peripheral artery disease, peripheral vascular disease, cerebrovascular disease, and any acute ischemic cardiovascular event.

In one embodiment of the invention, the method as described here above is for assessing the progression of a cardiovascular disease in a subject in need thereof.

In another embodiment of the invention, the method as described here above is for monitoring the effectiveness of a treatment for a cardiovascular disease. The efficacy of the treatment will be reflected by changes in the measurements of the cardiovascular risk factors. If a treatment has a desired effect, the measurements and thus the combined value of the cardiovascular risk factors will be lower compared to the measurements and combined value obtained before the treatment.

In another embodiment of the invention, the method as described here above is for selecting a treatment regimen for a subject diagnosed with or at risk for a cardiovascular disease.

Another object of the invention is a kit for identifying whether a subject has or is at risk of having or developing a cardiovascular disease and/or a cardiovascular event, comprising:

means for measuring sPLA2 activity and means for measuring OxPL/apoB.

In one embodiment, said kit further comprises means for combining the measurements in order to obtain a combined value.

Said means for combining the measurements of the cardiovascular risk factors are algorithms allowing statistical analysis such as DA (i.e. Linear-, Quadratic-, Regularized Discriminant Analysis), Kernel Methods (i.e. SVM), Nonparametric Methods (i.e. k-Nearest-Neighbor Classifiers), PLS (Partial Least Squares), Tree-Based Methods (i.e. Logic Regression, CART, Random Forest Methods, Boosting Methods), or Generalized Linear Models (i.e. Logistic Regression).

In another embodiment, said means for measuring sPLA2 activity are a sPLA2 buffer, a compound liable to be hydrolyzed by sPLA2, the hydrolytic products of which can be directly or indirectly quantified, a control sPLA2 activity sample.

According to said embodiment, the compound liable to be hydrolyzed by sPLA2 is a natural or non natural substrate of the enzyme. In case the hydrolysis products are not quantifiable by themselves, compounds which can react with these products and which yield quantifiable compounds can be used, such a method is an indirect quantification. In general, the compound liable to be hydrolysed by sPLA2 is a phospholipid or a phospholipid analogue comprising a fluorogenic or a chromogenic moiety. For example, said phospholipid is a glycerophospholipid which is substituted in position 2 by a fluorescent acyl; such as 1-hexadecanoyl-2-(1-pyrenedecanoyl)-sn-glycero-3-phosphomethanol or the fluorescent acyl 1-pyerenedecanoyl, the substrate for horseradish peroxidase being for example 3,3',5,5' tetramethyl-benzidine (TMB).

Fluorescent acyls liable to be used according to the invention are for example acyls substituted by fluorescent groups well known in the art, such as pyrene or fluoresceine. Alternatively, radioactive glycerophospholipids can be used, such as glycerophospholipids substituted in position 2 by radioactive acyls or radioactive phosphatidyl ethanolamine. The control sPLA2 activity sample comprises for example bee venom sPLA2.

In another embodiment, said means for measuring OxPL/apoB are

- an antibody that interacts specifically with OxPL such as for example E06, T15 or DLH3 and
- an antibody that interacts specifically with apoB such as for example MB47,
- optionally a control OxPL sample.

According to this embodiment, said control OxPL sample may be a sample containing a phosphorylcholine (PC). The PC can be used alone, or linked to a carrier protein, such as bovine serum albumin (BSA) or keyhole limpet hemocyanin (KLH).

In another embodiment of the invention, said kit may further comprise means for measuring at least one cardiovascular risk factor selected in the group of Framingham Risk Score (FRS), CRP, IgM IC of apoB100 or IgM MDA-LDL and LpPLA-2.

According to said embodiment, the Framingham Risk Score (FRS) is determined by method known in the art, such as the method described in Wilson PW et al. (Circulation. 1998 May 12;97(18):1837-47) and D'Agostino et al. (JAMA: The Journal of the American Medical Association. 2001;286: 180-187), which are incorporated by reference.

According to said embodiment, said means for measuring CRP are for example:

- a CRP buffer
- a monoclonal antibody that interacts specifically with CRP,
- an enzyme-conjugated antibody specific for CRP,
- a control CRP level.

According to said embodiment, said means for measuring IgM IC of apoB100 o are for example:

- an IgM of apoB100 buffer,
- a chemiluminescent reagent
- a monoclonal antibody specific for human apoB100,
- a alkaline phosphatase-labelled anti human IgM,
- a control IgM IC of apoB100 level sample.

According to said embodiment, said means for measuring IgM MDA-LDL are for example:

- an MDA-LDL buffer,
- a chemiluminescent reagent
- a alkaline phosphatase-labelled anti human IgM,
- a control IgM MDA-LDL of apoB100 level sample.

According to said embodiment, said means for measuring Lp-PLA-2 are for example:

- a compound which reduces active thiol(s) in a sample, and
- a substrate converted to a free thiol product in the presence of enzymatically active Lp-PLA2.

Optionally, said means may further comprises an antibody that interacts specifically with Lp-PLA2 such as for example the monoclonal antibody 2C10, 4B4, B200, B501, 90D1E, 90E3A, 90E6C, 90G11D, or 90F2D.

For example, said compound which reduces active thiol(s) and said substrate converted to a free thiol product in the presence of enzymatically active Lp-PLA2 are described in WO2005074604, which is incorporated by reference.

According to said embodiment, said means for measuring sPLA2 mass are for example:

- a sPLA2 mass buffer
- a monoclonal antibody that interacts specifically with sPLA2-IIA,
- an enzyme-conjugated antibody specific for sPLA2 IIA,
- a control sPLA2 mass level.

DESCRIPTION OF THE FIGURES

FIG. 1: Baseline characteristics of study participants.

FIG. 2: Unadjusted odds ratios of incident coronary artery disease during follow up according to combined tertiles of sPLA2 activity or Lp-PLA2 activity and OxPL/apoB.

FIG. 3: Adjusted odds ratios of incident coronary artery disease during follow up according to combined tertiles of sPLA2 activity or Lp-PLA2 activity and OxPL/apoB.

FIG. 4: Area under ROC for FRS and combination with at least one of OxPL/apoB, Lp-PLA2 activity, sPLA2 activity and CRP.

The tertile cutoffs for OxPL/apoB are <1150 RLU, 1151-2249 RLU and >2249 RLU, for sPLA2 activity levels <4.05 nmol/min per ml, 4.05-4.83 nmol/min per ml and >4.83 nmol/min per ml, for sPLA2 mass levels <6.80 mg/dl, 6.80-11.29 mg/dl and >11.19 mg/dl, and for Lp-PLA2 activity <44.05 nmol/min per ml, 44.05-56.23 nmol/min per ml and >56.23 nmol/min per ml.

FIG. 6: Area under ROC for FRS and combination with at least one of OxPL/apoB, Lp-PLA2 activity, sPLA2 activity and CRP.

Figure 7:
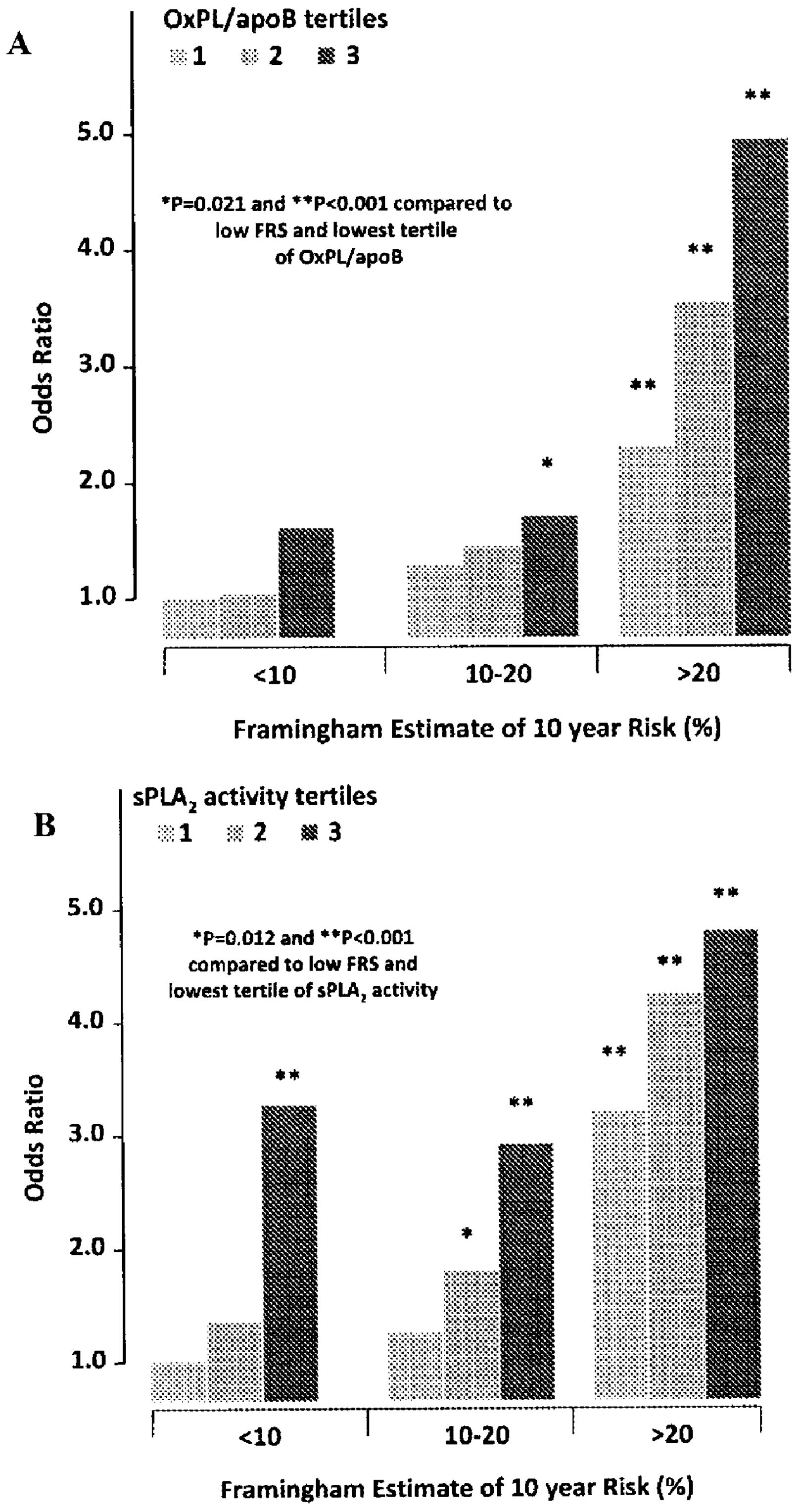
Figure 7:
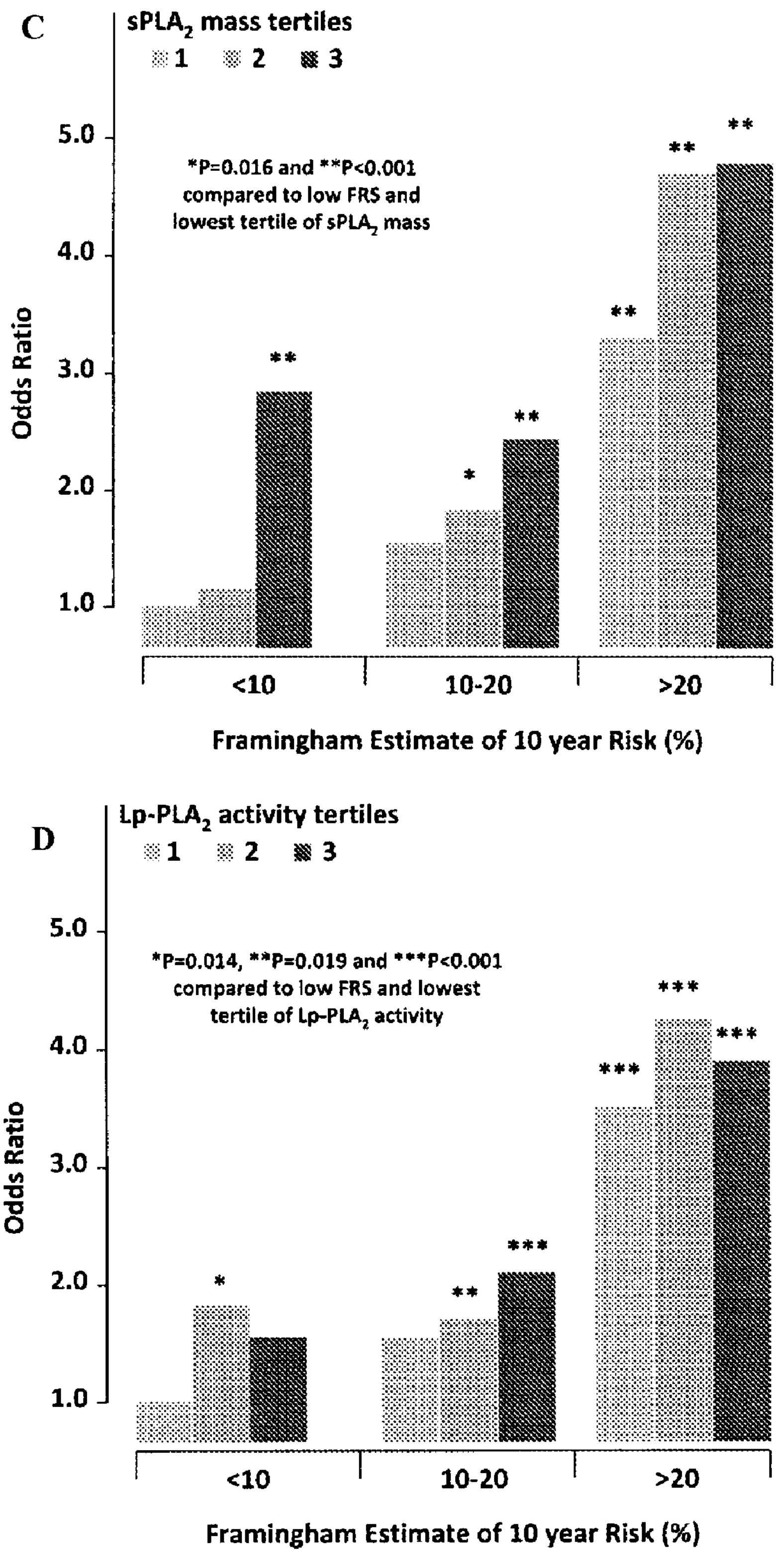

FIG. 7: Relationship between tertile groups of OxPL/apoB (<1150, 1151-2249 and >2249 RLU, (A)), sPLA2 activity (<4.05, 4.05-4.83 and >4.83 nmol/min per ml; (B)), sPLA2 mass (<6.80, 6.80-11.29 and >11.19 mg/dl; (C)), Lp-PLA2 activity (<44.05, 44.05-56.23 and >56.23 nmol/min per ml; (D)), and future CAD risk within each Framingham Risk Score Group. Framingham Risk Score was calculated as low risk (<10% risk of events over 10 years), moderate risk (10% to 20%), and high risk (>20%). The p-values in the figure represent comparison of each tertile of the respective biomarkers with the lowest tertile in the low FRS category of each biomarker.

EXAMPLES

Methods

Detailed description of the European Prospective Investigation Into Cancer and Nutrition (EPIC-Norfolk) follow-up study have been published previously (Day N. et al., Br. J. Cancer, 1999; 80 Suppl. I: 95-103). Briefly, this prospective population study of 25,663 men and women recruited from age-sex registers of general practices in Norfolk, aged between 45 and 79 years, was designed to investigate dietary and other determinants of cancer. The participants completed a baseline questionnaire survey between 1993 and 1997, attended a clinic visit and were followed up to November 2003, an average of about 6 years. All individuals have been flagged for death certification at the UK Office of National Statistics, with vital status ascertained for the entire cohort. In addition, participants admitted to hospital were identified using their unique National Health Service number by data linkage with the East Norfolk Health Authority database, which identifies all hospital contacts throughout England and Wales for Norfolk residents. The study was approved by the Norwich Health Authority Ethics Committee, and all participants provided written informed consent.

Study Population (FIG. 1)

A nested-case control study was performed among participants in the Epic-Norfolk study. Case ascertainment has been described in detail elsewhere (Boekholdt, S. M., Circulation, 2004; 110:1418-1423. Briefly, 25,663 healthy men and women, aged between 45 and 79 years, were recruited from age—sex registers of general practices in Norfolk. The participants completed a baseline questionnaire survey between 1993 and 1997, attended a clinic visit and were followed for an average of 6 years. Individuals who reported a history of heart attack or stroke at the baseline visit were excluded. Case ascertainment has been described previously. All individuals have been flagged for death certification at the UK Office of National Statistics, with vital status ascertained for the entire cohort. In addition, participants admitted to hospitals were identified using their National Health Service number by data linkage with the East Norfolk Health Authority database, which identifies all hospital contacts throughout England and Wales for Norfolk residents. Participants were identified as having CAD during follow-up if they had a hospital admission and/or died with CAD as the underlying cause. CAD was defined as codes 410 to 414 according to the International Classification of Diseases 9th revision. These codes encompass the clinical spectrum of CAD such as unstable angina, stable angina, and myocardial infarction. Controls were study participants who remained free of any cardiovascular disease during follow-up. Were excluded all individuals who reported a history of heart attack or stroke at the baseline clinic visit. Two controls to each case by sex, age (within 5 years) and time of enrolment (within 3 months) were matched. Data on non-cardiac events has not been collected. The study was approved by the Norwich Health Authority Ethics Committee, and all participants provided written informed consent.

Study Measurements

Blood samples were stored at −80° C. at the Department of Clinical Biochemistry, University of Cambridge. Serum levels of total cholesterol, HDL-cholesterol (HDL-C) and triglycerides were measured on fresh samples with the RA 1000 (Bayer Diagnostics, Basingstoke, UK), and LDL-cholesterol (LDL-C) levels were calculated with the Friedewald formula (Friedewald WT. et al., CHn Chem. 1972;18:499-502. CRP levels were measured with a sandwich-type ELISA as previously described (Bruins P. et a \. Circulation. 1997;96:3542-3548).

Serum sPLA2 activity was measured by a selective fluorimetric assay of Radvanyi et al. (Anal Biochem. 1989;177: 103-109), as modified by Pernas et al. (Biophys Res Commun. 1991;178:1298-1305). The sPLA2 activity was measured using fluorescent substrate 1-hexadecanoyl-2-(1-pyrenedecanoyl)-sn-glycero-3 phosphomethanol, sodium salt (Interchim, Montlucon, France) as previously described (Mallat Z. et al. J Am Coll Cardiol. 2005;46: 1249-1257). One hundred percent hydrolysis of the fluorescent substrate was measured using 0.1 unit PLA2 from Bee venom (Sigma Chemical Co., France). The hydrolysis of substrate in the absence of plasma was used as negative control and deduced from PLA2 activity. All the samples were tested in duplicate and plasma activity was expressed as nmole/min/ml. The minimum detectable activity was 0.10 nmole/min/ml. The imprecision of sPLA2 activity fluorimetric assay was determined by measurement of samples with low (1.25 nmol/min/ml) and high (9.5 nmol/min/ml) sPLA2 activity. Within-batch CVs ranged from 2.7% (low-activity sample) to 3.2% (high-activity sample) and the between-batch CV was 5.7%.

OxPL/apoB levels were measured with antibody E06 as in Tsimikas et al (Current Opinion in Lipidology, 2008, 19:369-377, which is incorporated by reference).

All the samples were analyzed in random order to avoid systemic bias. Researchers and laboratory personnel were blinded to identifiable information, and could identify samples by number only.

Statistical Analysis

Baseline characteristics were compared between cases and matched controls taking into account the matching between them. A mixed effect model was used for continuous variables and conditional logistic regression was used for categorical variables. Because triglycerides, CRP, OxPL/apoB, sPLA2 antigen levels and sPLA2 activity had a skewed distribution, values were log-transformed before being used as continuous variables in statistical analyses; however, in the tables, untransformed medians and corresponding intertertile ranges are shown.

Tertiles were based on the distribution in the controls. For sex-specific analyses, sex-specific tertiles were used, and for pooled analyses, quartiles based on the sexes combined were used.

In addition, Pearson correlation coefficients were calculated to assess the relationship between sPLA2 activity as a continuous variable and other continuous biomarkers of risk. Odds ratios and corresponding 95% confidence intervals (95% CIs) as an estimate of the relative risk of incident CAD were calculated using conditional logistic regression analysis.

The lowest sPLA2 activity or the lowest Lp-PLA2 activity and the lowest OxPL/apoB tertiles were used as reference category.

Odds Ratios were adjusted for the following cardiovascular risk factors: body mass index, diabetes, systolic blood pressure, LDL-C, HDL-C, and smoking (never, previous, current).

Odds Ratios were also adjusted for the FRS score. The Framingham Risk Score was calculated using a previously reported algorithm, which takes into account age, sex, total cholesterol, HDL-C, systolic and diastolic blood pressure, smoking and the presence of diabetes (Wilson P. W. et al., Circulation. 1998;97:1837-1847). Statistical analyses were performed using SPSS software (version 12.0.1; Chicago, III).A P-value $<0.05$ was considered to indicate statistical significance.

Results

Combined Measurements of sPLA2 Activity and OxPL/apoB to Assess the Risk of Incident CAD We selected cases that developed CHD during follow-up and selected controls that remained free of cardiovascular disease, and were matched to cases by sex, age and enrolment time. The risk of CHD events was significantly potentiated by elevated activity of sPLA2 and Lp-PLA2 and by elevated OxPL/apoB. People in the highest tertiles of both OxPL/apoB and LpPLA2 activity had an odds ratio of 2.22 (1.51-3.27) and patients in the highest tertiles of both OxPL/apoB and sPLA2 activity had an odds ratio of 4.34 (2.84-6.64) ($p<0.0001$ for both compared to those in lowest tertiles for both) (FIG. 2 and FIG. 3 for OR's adjusted for FRS score).

Figure 5:
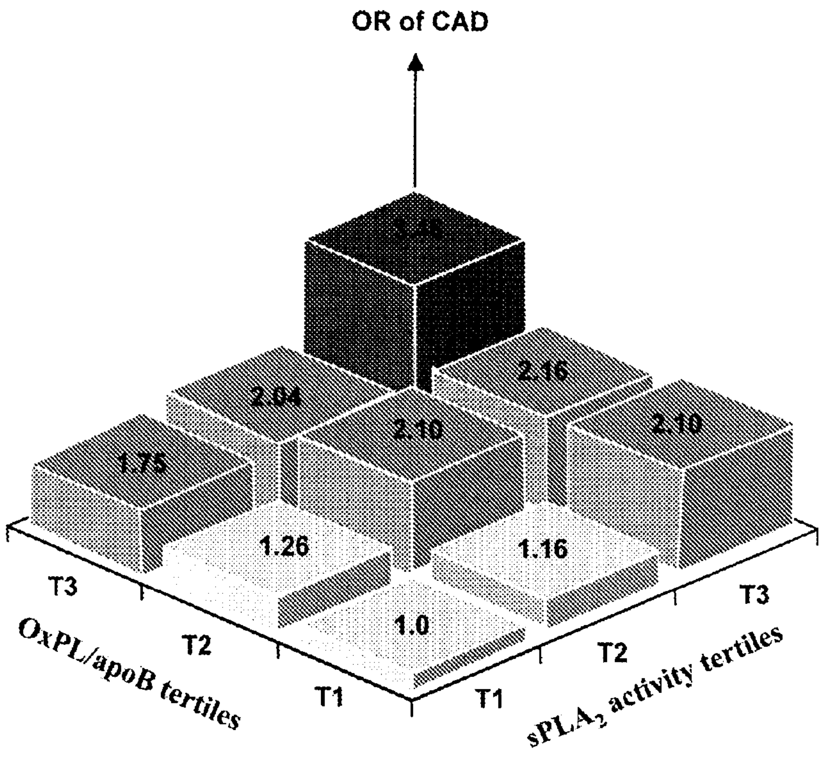
FIG. 5: Odds ratios for CAD based on tertiles of OxPL/apoB and sPLA2 activity, sPLA2 mass and Lp-PLA2.

Results shown in FIG. 5 are based on 763 cases and 1397 controls wherein all subject characteristics listed in table 1 were available.

FIG. 5 shows that subjects in the highest tertiles for both sPLA2 activity and OxPL/apoB had a significantly elevated risk of future CAD, with an OR of 3.46 (2.22-5.42) compared to subjects in the lowest tertiles. A similar but weaker relationship was noted for the highest tertiles of sPLA2 mass and OxPL/apoB (OR 2.39 (1.58-3.61)).

Area under receiver operating curves revealed significantly increased values by adding OxPL/apoB and sPLA2 activity to traditional risk factors and the FRS (FIG. 4).

Results shown in FIG. 6 are based on 763 cases and 1397 controls wherein all subject characteristics listed in table 1 were available and confirm that adding OxPL/apoB and sPLA2 activity to traditional risk factors and the FRS increases the predictive value.

To assess whether oxidative biomarkers provided additional predictive value to the FRS, tertiles of OxPL/apoB, sPLA2 mass, sPLA2 activity and Lp-PLA2 activity were evaluated within each FRS risk estimate (FIG. 7). In the low FRS categories, the OxPL/apoB measure did not provide additional predictive value, but sPLA2 mass and activity showed a near tripling of the odds ratio. However, in the high FRS estimates, OxPL/apoB more than doubled the odds ratio for predicting new cardiovascular events, sPLA2 mass and activity was slightly less predictive. The combination of OxPL/apoB and sPLA2 activity was particularly useful in reflecting risk adjustment among the FRS categories. For example, in the low FRS category, compared to the lowest tertiles, the highest tertiles of OxPL/apoB and $sPLA_2$ activity were associated with an OR (95% CI) of 8.48(2.98-24.16, P<0.001), in the medium FRS category 5.01(2.28-11.41, P<0.001) and in the high FRS category 14.35(6.2133.17, P<0.001).

This case-control study nested within the prospectively followed EPIC-Norfolk cohort demonstrates that elevated baseline levels of OxPL/apoB are strongly associated with increased risk of future fatal and non-fatal CAD events. Furthermore, increased levels of phospholipases involved in the metabolism of OxPL, particularly sPLA2 activity, potentiated the risk of fatal and non-fatal CAD events mediated by either OxPL/apoB.

In the Bruneck study, the hazard ratio of cardiovascular diseases mediated by OxPL/apoB levels was increased from about 2 to 4 by Lp-PLA2 activity (Kiechl et al., *Arterioscler Thromb Vasc Biol.* 2007;27:1788-1795). However, a weak association was noted in this EPIC-Norfolk study. The explanations are not obvious, but may relate to differences in methodology (prospective versus case control) or more likely to the size of the study (82 events in the Bruneck study versus 763 events in the EPIC-Norfolk study).

The invention claimed is:

1. A method of identifying a subject having or at risk of having or developing a cardiovascular disease and/or a cardiovascular event, comprising:

measuring, in a blood sample obtained from said subject, at least two cardiovascular risk factors:

a) secretory phospholipases A2 (sPLA2) activity and b) oxidized phospholipids on apolipoprotein B-100 particles (OxPL/apoB), combining said measurements, the combined value of sPLA2 activity and OxPL/apoB being indicative of having or a risk of having or developing a cardiovascular disease and/or cardiovascular event.

2. The method according to claim 1, wherein said combined value of sPLA2 activity and OxPL/apoB is compared to a reference value.

3. The method according to claim 1, further comprising measuring at least one cardiovascular risk factor selected in the group of Framingham Risk Score (FRS), C-reactive protein (CRP), IgM IC of apoB100 or IgM MDA-LDL and lipoprotein-associated phospholipase A2(Lp-PLA2).

4. The method according to claim 1, wherein sPLA2 activity, OxPL/apoB and FRS are measured.

5. The method according to claim 1, wherein sPLA2 activity, OxPL/apoB, FRS and CRP are measured.

6. The method according to claim 1, wherein said cardiovascular disease and/or cardiovascular event is Metabolic Syndrome, Syndrome X, atherosclerosis, atherothrombosis, coronary artery disease, stable and unstable angina pectoris, stroke, diseases of the aorta and its branches (such as aortic thrombosis or aortic aneurysm), peripheral vascular disease, cerebrovascular disease, and any acute ischemic cardiovascular event.

7. The method according to claim 1, wherein OxPL/apoB is measured in an immunoassay using an antibody that interacts with OxPL and an antibody that interacts with apoB.

8. The method according to claim 1, wherein sPLA2 activity is measured in a fluorimetric assay using a substrate for sPLA2.

9. The method according to claim 1, for monitoring the efficacy of a treatment for a cardiovascular disease.

10. The method according to claim 2, further comprising measuring at least one cardiovascular risk factor selected from the group consisting of Framingham Risk Score (FRS), CRP, IgM IC of apoB100 or IgM MDA-LDL and LpPLA-2.

* * * * *